United States Patent
Nakano

(10) Patent No.: US 9,066,830 B2
(45) Date of Patent: Jun. 30, 2015

(54) APPARATUS TO MANUFACTURE ABSORBENT BODY

(75) Inventor: Takumi Nakano, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 338 days.

(21) Appl. No.: 13/574,843

(22) PCT Filed: Dec. 3, 2010

(86) PCT No.: PCT/JP2010/071639
§ 371 (c)(1),
(2), (4) Date: Oct. 5, 2012

(87) PCT Pub. No.: WO2011/092935
PCT Pub. Date: Aug. 4, 2011

(65) Prior Publication Data
US 2013/0014899 A1    Jan. 17, 2013

(30) Foreign Application Priority Data

Jan. 28, 2010   (JP) ................. 2010-017125

(51) Int. Cl.
  *B32B 41/00* (2006.01)
  *A61F 13/15* (2006.01)
(52) U.S. Cl.
  CPC ..... *A61F 13/15642* (2013.01); *A61F 13/15634* (2013.01); *A61F 13/15626* (2013.01); *A61F 13/15617* (2013.01); *B32B 41/00* (2013.01); *A61F 13/1565* (2013.01)
(58) Field of Classification Search
  CPC .. B02C 13/28663; B32B 41/00; B32B 41/02; D01G 7/06; D21B 1/061; D21B 1/066; D21B 1/068; D21C 7/02; G01G 15/06; A61F 13/15617; A61F 13/15626; A61F 13/15634; A61F 13/15642; A61F 13/1565

USPC ............. 156/352, 361, 366, 378; 162/20, 28, 162/259, 262, 267; 19/145.5
See application file for complete search history.

(56) References Cited

U.S. PATENT DOCUMENTS 3,519,211 A    7/1970   Sakulich et al.
3,825,194 A *  7/1974   Buell ........................... 241/191
(Continued)

FOREIGN PATENT DOCUMENTS

CN        1954108 A    4/2007
JP       52015606 A    2/1977
(Continued)

OTHER PUBLICATIONS

International Search Report for PCT/JP2010/071639, dated Mar. 1, 2011.
(Continued)

*Primary Examiner* — George Koch
(74) *Attorney, Agent, or Firm* — Lowe Hauptman & Ham, LLP

(57) ABSTRACT

An apparatus for manufacturing an absorbent body includes: a sheet supplying mechanism for supplying a sheet from a sheet roll; a crusher for crushing the sheet into a fibrous matter by scraping a reeling-out tip end of the reeled out sheet; and a fiber stacking device for forming the absorbent body in a predetermined shape by laminating the fibrous matter to be sent out from the crusher. When switching a supply of the sheet to the crusher from one to another sheet supplying mechanism, at least two sheet supplying mechanisms supply the sheet to the crusher over a predetermined period including a period in which the one sheet supplying mechanism decreases a sheet reeling-out speed, in correspondence with the period in which the one sheet supplying mechanism decreases the sheet reeling-out speed, the other sheet supplying mechanism increases a sheet reeling-out speed.

16 Claims, 9 Drawing Sheets

(56) References Cited

U.S. PATENT DOCUMENTS

| | | | |
|---|---|---|---|
| 4,064,599 | A | 12/1977 | Neuenschwander |
| 4,241,881 | A | 12/1980 | Laumer |
| 4,673,136 | A | 6/1987 | Bianco et al. |
| 2002/0124354 | A1 | 9/2002 | Pferdmenges et al. |
| 2007/0227679 | A1 | 10/2007 | Maruhata |

FOREIGN PATENT DOCUMENTS

| | | | |
|---|---|---|---|
| JP | 56101961 A | 8/1981 | |
| JP | 2002201533 A | 7/2002 | |
| JP | 2006063467 A | 3/2006 | |
| JP | 2006063468 A | 3/2006 | |
| JP | 2006081888 A | 3/2006 | |
| JP | 2007002371 A | 1/2007 | |
| JP | 2009112347 A | 5/2009 | |
| JP | 2010035701 A | 2/2010 | |

OTHER PUBLICATIONS

Extended European Search Report issued Dec. 12, 2013, corresponds to European patent application No. 10844689.9.

Office Action dated Jan. 6, 2014, corresponds to Chinese patent application No. 201080062527.7.

* cited by examiner

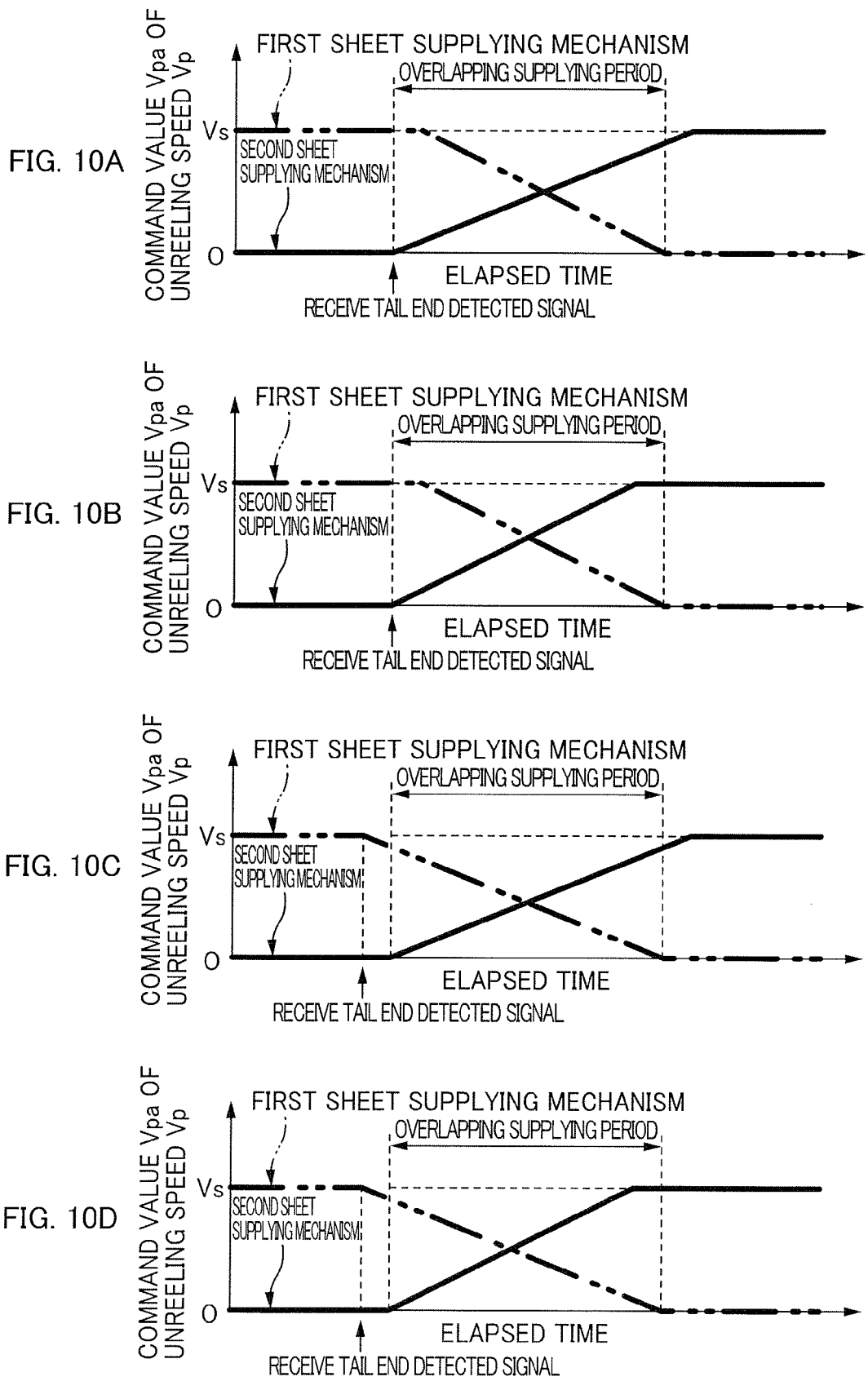

APPARATUS TO MANUFACTURE ABSORBENT BODY

RELATED APPLICATIONS

The present application is a National Phase of International Application Number PCT/JP2010/071639, filed Dec. 3, 2010, and claims priority from Japanese Application Number 2010-017125, filed Jan. 28, 2010.

TECHNICAL FIELD

The present invention relates to an apparatus to manufacture an absorbent body of an absorbent article such as a disposable diaper.

BACKGROUND ART

Conventionally, in a manufacturing line of an absorbent article such as a disposable diaper, as shown in a schematic side view of FIG. 1, an absorbent body 1 that absorbs a liquid such as a waste fluid has been produced. The absorbent body 1 is produced by crushing a pulp sheet 3 with a crusher 20 into pulp fibers 4, and laminating these pulp fibers 4 into a predetermined shape such as a substantially rectangular parallelepiped with a fiber stacking device 30 (PTL 1).

CITATION LIST

Patent Literature

PTL 1 Patent Application Laid-open Publication No. 2009-112347

SUMMARY OF INVENTION

Technical Problem

Supply of the pulp sheet 3 to the crusher 20 is generally performed by reeling out the pulp sheet 3 from a pulp sheet roll 5 (a roll shape made by reeling up the pulp sheet 3). In this reeling Out, a pair of top and bottom pinch rolls 55, 55 is used. In other words, when the pair of pinch rolls 55, 55 drivingly rotates in a state sandwiching the pulp sheet 3, the pulp sheet 3 is drawn out from the pulp sheet roll 5.

Then, when all the pulp sheet 3 from the pulp sheet roll 5 has been reeled out and cut, as shown in FIG. 2A, to the tail end 3TE of the pulp sheet 3 is brought a tip end 3LE of a pulp sheet 3 of a new pulp sheet roll that is waiting, and the new pulp sheet 3 is supplied to the pinch rolls 55, 55. In this way, the pulp sheet 3 is to be continuously supplied to the crusher 20.

The new pulp roll sheet 5 is generally a heavy object of approximately 1 ton, however, and thus a rotating inertia when starting the reeling out of this pulp sheet roll 5 is excessively large. Thus, when starting the reeling out, slipping of the pinch rolls 55, 55 and the pulp sheet 3, or the pinch rolls 55, 55 not being able to increase speed as desired due to a torque deficiency when starting the driving motor of the pinch rolls 55, 55 or the like occur, thus causing, as shown in FIG. 2B, a large interval in between the tail end 3TE of the leading old pulp sheet 3 and the tip end 3LE of the latter new pulp sheet 3. As a result, the supply of the pulp sheet 3 to the crusher 20 tends to become non-continuous.

Further, as shown in FIG. 1, the crusher 20 scrapes and crushes the tip end 3LE of the pulp sheet 3 with a rotating blade 22 inside the crusher and attenuates it. Thus, as in FIG. 2B, when the tail end 3TE of the former pulp sheet 3 goes through the pinch rolls 55, 55, the former pulp sheet 3 is pulled in rapidly into the crusher 20 with the rotating blade 22 of the crusher 20, and this pull-in phenomenon also promotes enlargement of the interval between the above-mentioned tail end 3TE of the former pulp sheet 3 and the tip end 3LE of the new pulp sheet 3.

Then, when the supply of the pulp sheet 3 becomes discontinuous in this way, the supply of the pulp fibers 4 to the fiber stacking device 30 that is downstream also becomes discontinuous, and as a result an absorbent body 1 deficient in the pulp fibers 4 is produced, and it becomes a reason for reduction in yields of products.

On the other hand, as an idea to prevent discontinuous supply to the above-mentioned crusher 20, as shown in FIG. 2C, the tail end 3TE of the former pulp sheet 3 and the tip end 3LE of the new pulp sheet 3 can be polymerized and joined on top of each other. With this method, however, the process to join the ends in a polymerized state becomes necessary, and the process steps increase, and when the polymerized section is supplied to the crusher 20, the pulp sheet 3 is overly (excessively) supplied. As a result, with the downstream fiber stacking device 30, an absorbent body 1 with excessive pulp fibers 4 is produced, and as expected becomes a cause for reduction in yields of products.

The present invention has been made in view of the above conventional problems, and an object is to provide an apparatus that manufactures an absorbent body that can suppress fluctuations in a supply amount of a sheet which may occur when switching from a former sheet roll to a new sheet roll the supply of the sheet from a sheet roll such as a pulp sheet roll to a crusher.

Solution to Problem

An advantage achieved by some aspects of the present invention is an apparatus that manufactures an absorbent body including:
  a sheet supplying mechanism that reels out and supplies a sheet from a sheet roll made by reeling up the sheet in a roll shape;
  a crusher that crushes the sheet into a fibrous matter by scraping a reeling-out tip end of the sheet that has been reeled out; and
  a fiber stacking device that forms the absorbent body in a predetermined shape by laminating the fibrous matter to be sent out from the crusher,
  wherein at least two sheet supplying mechanisms are included,
  when switching a supply of the sheet to the crusher from one sheet supplying mechanism to another sheet supplying mechanism, both sheet supplying mechanisms supply the sheet to the crusher over a predetermined period,
  the predetermined period includes a period in which the one sheet supplying mechanism decreases a reeling-out speed of the sheet,
  in correspondence with the period in which the one sheet supplying mechanism decreases the reeling-out speed of the sheet, the other sheet supplying mechanism increases a reeling-out speed of the sheet.

Other features of the inventions will become clear from the description in this specification and accompanying drawings.

Advantageous Effects of Invention

With this invention, fluctuations in the supply amount of the sheet which may occur when switching a supply of the sheet from the sheet roll to the crusher from the former sheet roll to the new sheet roll can be suppressed.

BRIEF DESCRIPTION OF DRAWINGS

FIGS. 10A to 10D are timing line diagrams showing examples of other switching operations.

DESCRIPTION OF EMBODIMENTS

Figure 1:
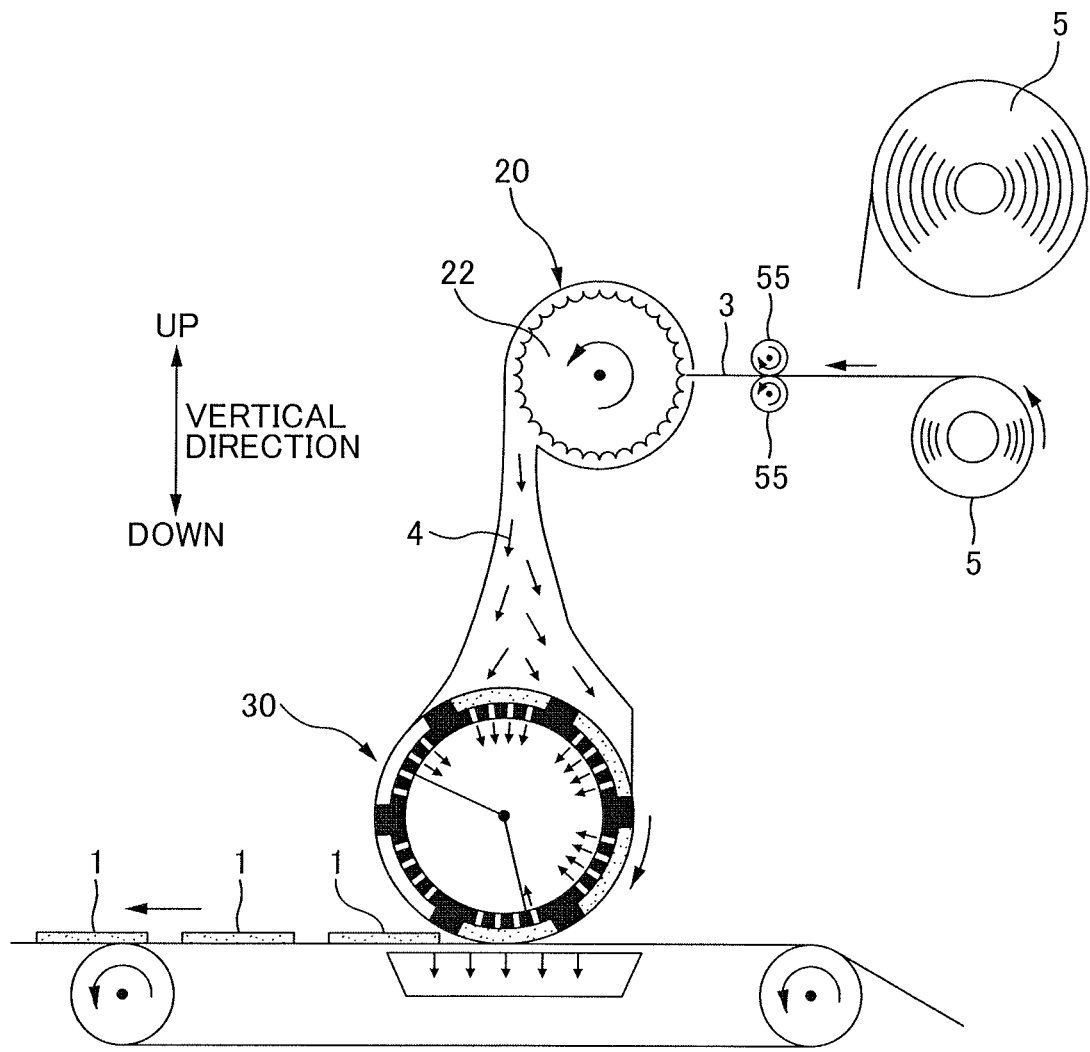
FIG. 1 is a schematic side view of a conventional example of an apparatus that manufactures an absorbent body 1.
Figure 2A:
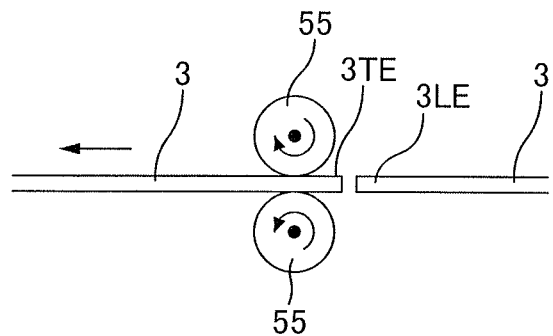
FIGS. 2A to 2C are explanatory diagrams of problems in the conventional example.
Figure 2B:
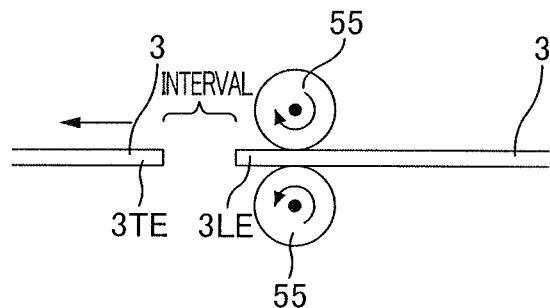
Figure 2C:
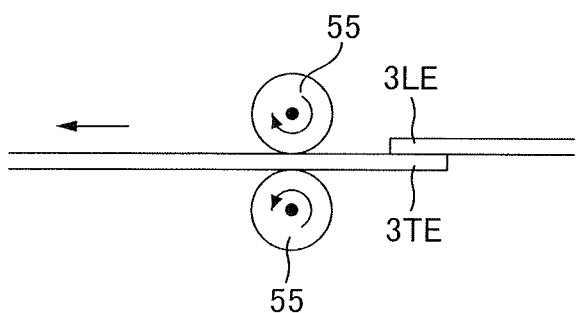

At least the following will become clear with the description in this specification and appended drawings.

An apparatus that manufactures an absorbent body including:
  a sheet supplying mechanism that reels out and supplies a sheet from a sheet roll made by reeling up the sheet in a roll shape;
  a crusher that crushes the sheet into a fibrous matter by scraping a reeling-out tip end of the sheet that has been reeled out; and
  a fiber stacking device that forms the absorbent body in a predetermined shape by laminating the fibrous matter to be sent out from the crusher,
  wherein at least two sheet supplying mechanisms are included,
  when switching a supply of the sheet to the crusher from one sheet supplying mechanism to another sheet supplying mechanism, both sheet supplying mechanisms supply the sheet to the crusher over a predetermined period,
  the predetermined period includes a period in which the one sheet supplying mechanism decreases a reeling-out speed of the sheet,
  in correspondence with the period in which the one sheet supplying mechanism decreases the reeling-out speed of the sheet, the other sheet supplying mechanism increases a reeling-out speed of the sheet.

With this apparatus that manufactures the absorbent body, the other sheet supplying mechanism increases the reeling-out speed, in correspondence with the period that the reeling-out speed of one sheet supplying mechanism decreases. Thus, the sum of the above reeling-out speeds cancel out the decrease and the increase in speed of each other, and it becomes generally the same as supplying the sheet at a constant reeling-out speed. Thus, fluctuations in the supply amount of the sheet to the crusher when switching from the one sheet supplying mechanism to the other sheet supplying mechanism can be suppressed.

With an apparatus that manufactures an absorbent body, wherein
  the one sheet supplying mechanism has a pair of pinch rolls that sandwich the sheet and drivingly rotate in order to reel out the sheet from the sheet roll, and a sensor that detects that an end of reeling out the sheet from the one sheet supplying mechanism is close,
  the apparatus to manufacture has a controller that controls the driving rotation of the pinch rolls,
  based on the detected signal from the sensor, the controller stops the driving rotation of the pinch rolls, before a tail end of the sheet passes through the pinch rolls.

With such an apparatus that manufactures the absorbent body, the driving rotation of the pinch rolls are stopped before the tail end of the sheet passes through the pinch rolls in the predetermined period, so that the above-mentioned pull-in phenomenon that may occur after the tail end of the sheet has passed through the pinch rolls can be effectively prevented. Therefore, the supply of the sheet to the crusher becoming discontinuous can be suppressed.

With an apparatus that manufactures an absorbent body, wherein
  the controller, after stopping the driving rotation of the pinch rolls in the predetermined period, drivingly rotates the pinch rolls in an opposite direction to a rotating direction before the driving rotation has been stopped.

With such an apparatus to manufacture an absorbent body, the sheet that is in a state in which the reeling out has stopped and that is in a state sandwiched with the pinch rolls can be sent in an opposite direction to the reeling out direction. Thus, the sheet can be easily discharged out of the apparatus.

With an apparatus that manufactures an absorbent body, wherein preferably
  the crusher includes a casing, a rotating blade, provided in the casing, that scrapes the reeling-out end, and one opening section provided to the casing,
  both the one sheet supplying mechanism and the other sheet supplying mechanism insert the sheet into the opening section.

With such an apparatus to manufacture an absorbent body, the supply condition of the sheet to the crusher can be made the same with the one sheet supplying mechanism and the other sheet supplying mechanism. In this way, the crushing condition of the sheets can be made uniform, and as a result a fibrous matter with the same crushed quality can be produced.

With an apparatus that manufactures an absorbent body, wherein preferably
  the one and the other sheet supplying mechanism each has a pair of pinch rolls that sandwiches the sheet and drivingly rotates in order to reel out the sheet from the sheet roll,
  the apparatus to manufacture has a controller that controls the driving rotation of the pinch rolls,
  in the period in which the one sheet supplying mechanism decreases the reeling-out speed of the sheet, the controller controls the driving rotation of the pinch rolls so that a reeling-out speed of the one sheet supplying mechanism becomes zero by gradually decreasing from a predetermined reference speed, and so that a reeling-out speed of the other sheet supplying mechanism becomes the reference speed by gradually increasing from zero.

With such an apparatus to manufacture an absorbent body, in correspondence to the gradual decrease of the reeling-out speed of the one sheet supplying mechanism, the reeling-out speed of the other sheet supplying mechanism is gradually increased, so that the fluctuations in the supply amount of the sheet to the crusher when switching from the one to the other sheet supplying mechanism can be suppressed.

With an apparatus that manufactures an absorbent body, wherein preferably in the period in which the one sheet supplying mechanism decreases the reeling-out speed of the sheet, the controller controls the driving rotation of the pinch rolls so that a sum of a reeling-out speed of the one sheet supplying mechanism and a reeling-out speed of the other sheet supplying mechanism is in a range of ±10% of the reference speed.

With such an apparatus that manufactures an absorbent body, the sum of the reeling-out speed of the one sheet supplying mechanism and the reeling-out speed of the other sheet supplying mechanism are made to be in a range of ±10% of the reference speed, so that the fluctuations in the supply amount of the sheet to the crusher when switching from the one to the other sheet supplying mechanism can be suppressed furthermore.

First Embodiment

Figure 3:
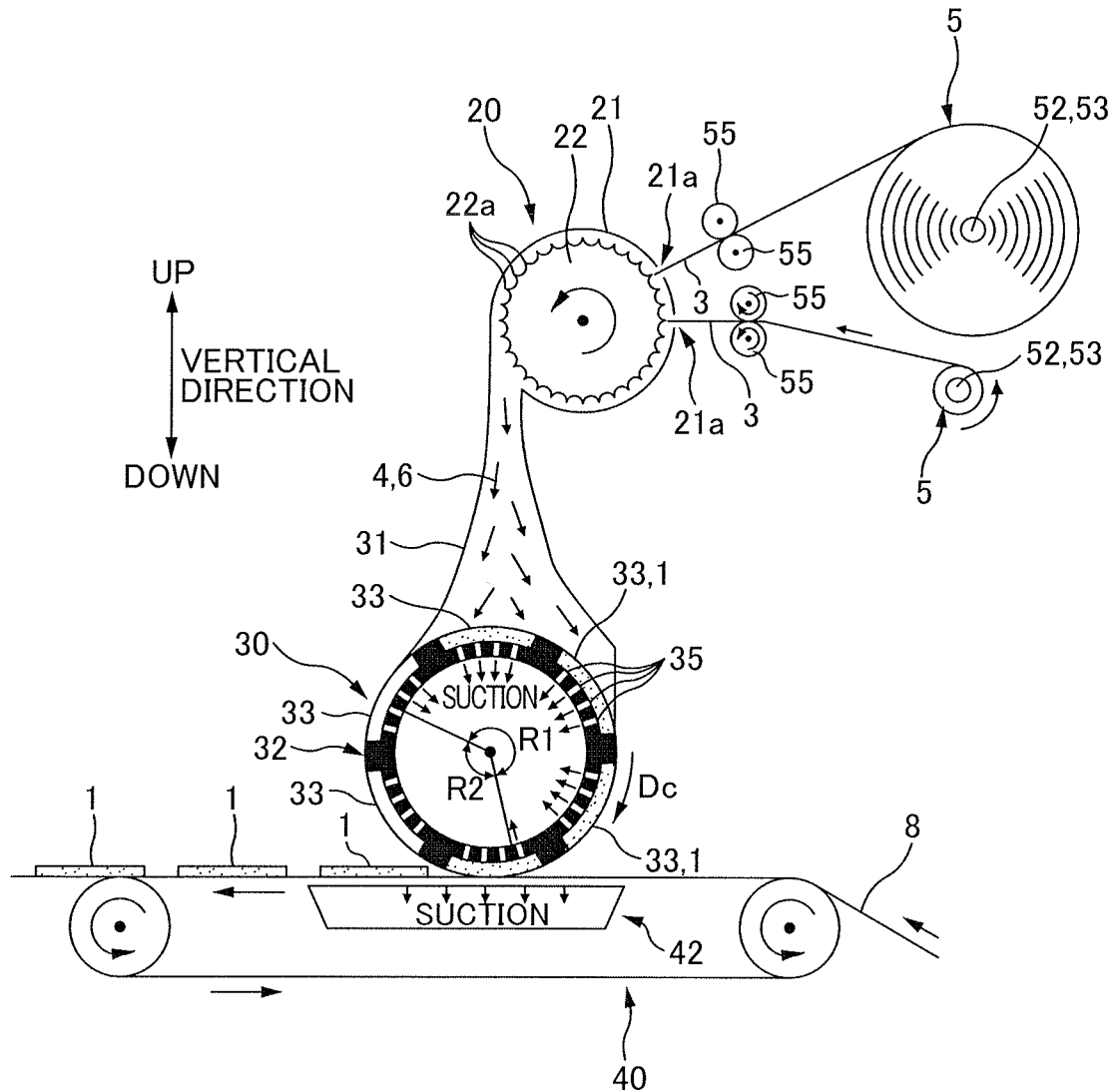
FIG. 3 is a schematic side view of an apparatus that manufactures an absorbent body 1 of a first Embodiment.

FIG. 3 is a schematic side view of an apparatus to manufacture an absorbent body 1 in a First Embodiment.

The apparatus that manufactures the absorbent body 1 includes a crusher 20 that crushes the pulp sheet 3 supplied continuously in a longitudinal direction of the pulp sheet 3 into pulp fibers 4 (corresponds to fibrous matter), and a fiber stacking device 30 that produces the absorbent body 1 by laminating the pulp fibers 4 to be sent from the crusher 20 into a predetermined shape such as a substantially rectangular body.

Note that, hereafter, a supplying direction of the pulp sheet 3 (a direction parallel to a paper plane of FIG. 3) is referred to as a "transporting direction" or an "MD direction", and a direction parallel in a width direction to the pulp sheet 3 is referred to as a "CD direction". Incidentally, the CD direction and the MD direction are orthogonal to each other, and the CD direction in FIG. 3 is a direction that penetrates the paper plane of FIG. 3.

The crusher. 20 has a casing 21 forming an outer section thereof. Inside the casing 21, a rotating blade 22 is provided. The rotating blade 22 has a plurality of cutting edges 22a, 22a . . . on a peripheral surface, and a rotating force is obtained from an appropriate driving source such as a motor, and the blade drivingly rotates at a constant speed around an axial center along the CD direction. In this way, the pulp sheet 3 placed inside from the placing opening 21a (corresponds to an opening section) of the casing 21 is crushed into the pulp fibers 4. The crushed pulp fibers 4 are sent out to the fiber stacking device 30 via a duct 31 that communicates a space inside the casing 21 with the fiber stacking device 30. In detail, inside the duct 31, an air flow 6 occurs towards the fiber stacking device 30, and with this air flow 6 the pulp fibers 4 are sent out to the fiber stacking device 30. This air flow 6 will be described later.

The fiber stacking device 30 has for example, a cylindrical rotating drum 32 as a body. The rotating drum 32 drivingly rotates along a circumferential direction Dc around an axial center facing the CD direction. Further, the peripheral surface of the rotating drum 32 is provided with a plurality of shaping dies 33, 33 in a predetermined pitch in the circumferential direction Dc, and a bottom surface of each shaping die 33 is formed with multiple suction holes 35, 35 . . . . Further, one end opening of the duct 31 described above is opposed to the peripheral surface of the rotating drum 32 and covers the peripheral surface over a predetermined range in the circumferential direction Dc. Therefore, the pulp fibers 4 to be sent from the crusher 20 are sent with the above-mentioned air flow 6 formed in the duct 31 by the suction from the suction holes 35 and deposited in the shaping die 33. In this way, the absorbent body 1 is formed in the shaping die 33 with the depositing direction as a thickness direction.

Note that, this suction is performed in a first range R1 including a range in which the shaping die 33 is opposed to the duct 31 in the circumferential direction Dc, but the suction is stopped and is not performed in a second range R2 including a range in which the shaping die 33 is opposed to a belt conveyor 40. Further, in the latter second range R2, the absorbent body 1 in the shaping die 33 is subsequently separated from inside the shaping die 33 by suction from a suction box 42 of the belt conveyor 40, and in this way the absorbent body 1 is handed over to a continuous sheet member 8 on the belt conveyor 40.

Figure 4:
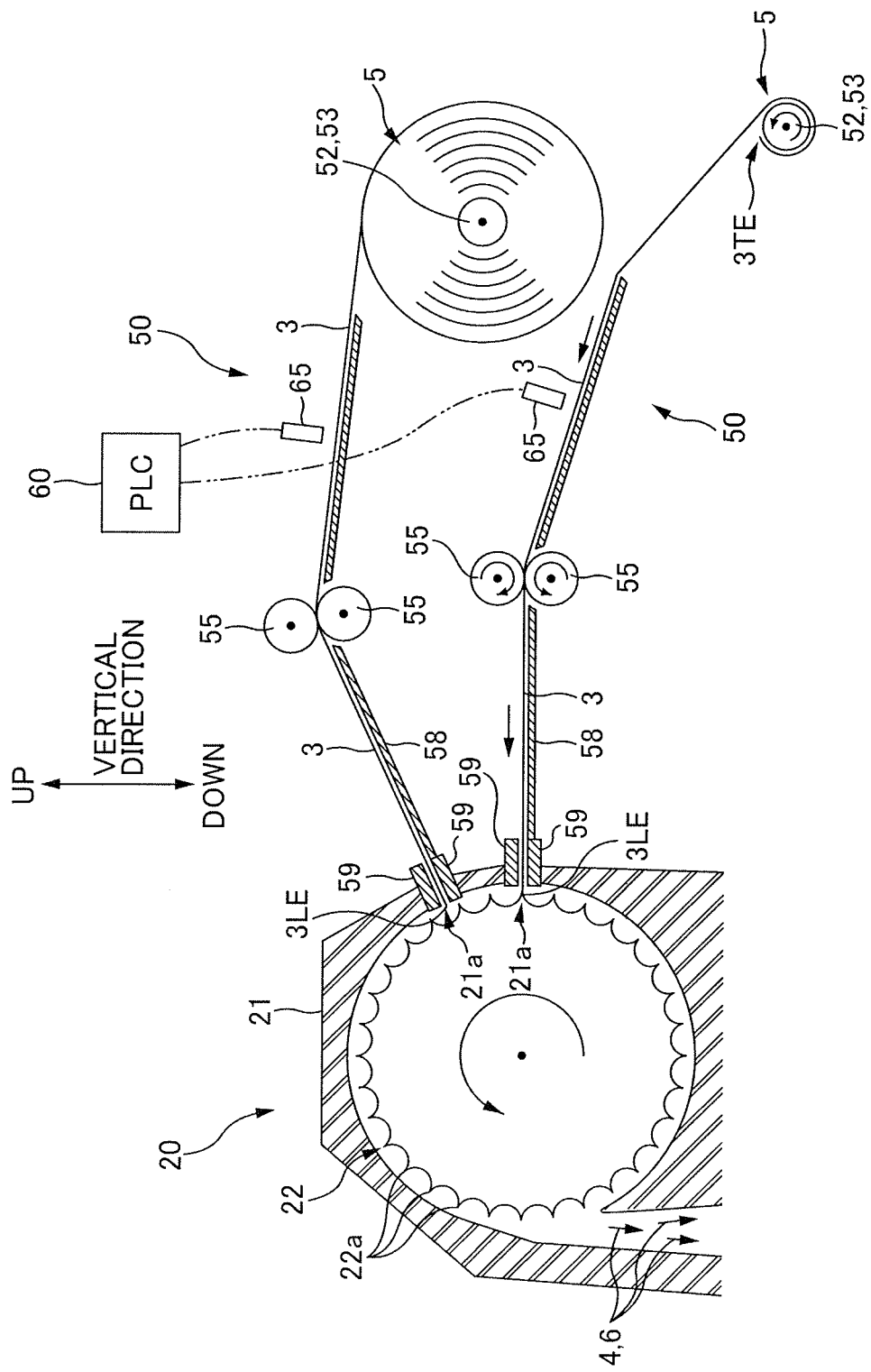
FIG. 4 is a schematic side view of sheet supplying mechanisms 50, 50, that supply a pulp sheet 3 to a crusher 20.

FIG. 4 is a schematic side view of the sheet supplying mechanisms 50, 50 that supply the pulp sheet 3 to the crusher 20. In this example, two sheet supplying mechanisms 50, 50 are provided as an example of a plurality of mechanisms in respect to one crusher 20. Both mechanisms have the same function, namely, the pulp sheet 3 is reeled out from the pulp sheet roll 5 (the pulp sheet 3 is reeled up and made into a roll shape) and supplied to the crusher 20. Basically the mechanisms are to be used alternatively. Namely, in the case one mechanism is supplying, the other remaining mechanism is waiting, and during this waiting the new pulp sheet roll 5 is set. Then, when the pulp sheet 3 is reeled out from the pulp sheet roll 5 of the supplying sheet supplying mechanism 50 and cut, the reeling out from the new pulp sheet roll 5 of the sheet supplying mechanism 50 that is waiting is started, and as a result of this the supply of the pulp sheet 3 is switched from the one sheet supplying mechanism 50 to the other sheet supplying mechanism 50. Then, by repeating the switching of this supplying, the pulp sheet 3 is continuously supplied to the crusher 20 without interruption.

As shown in FIG. 4, basically these sheet supplying mechanisms 50, 50 have substantially the same structure as each other. Namely, both sheet supplying mechanisms 50, 50 include a reel 52 that rotatably holds the pulp sheet roll 5, a pair of top and bottom pinch rolls 55, 55 that reels out the pulp sheet 3 from the pulp sheet roll 5 on the reel 52, and a guide plate 58 that guides the transporting of the pulp sheet 3 from the pinch rolls 55, 55 to the placement opening 21a of the crusher 20.

Further, the pulp sheet rolls 5, 5 held in each of the reels 52, 52 have basically the same specification as each other. Namely, the thickness (basis weight) and width of the pulp sheet 3 are unified to a same standard. Note that, the reel-up length does not have to be the same length.

The reel 52 has a core rod 53 that is inserted along a CD direction in a hole section in the reel-up center of the pulp sheet roll 5, and with the core rod 53 the pulp sheet roll 5 is supported rotatably.

The pinch rolls 55, 55 each have an axis of rotation along the CD direction. At least one roll 55 of these rolls 55, 55 is drivingly rotated with a servomotor that is not shown as the driving source. Further, at least one roll 55 of the pinch rolls 55, 55 is given a pressing force in a direction in which the rolls 55, 55 come close to each other with a pressing member that is not shown. Thus, the pinch rolls 55, 55 sandwich the pulp sheet 3 in an interval between the rolls and drivingly rotate, so that the pulp sheet 3 is reeled out from the pulp sheet roll 5.

The guide plate 58 is a plate shaped member, which is extended across from the pinch rolls 55 to the placing opening 21a of the casing 21 of the crusher 20. Then, with the upper surface thereof, the pulp sheet 3 is guided to the placing opening 21*a*. Note that, at an end section to the placing opening 21*a* side of the guide plate 58 is set a pair of top and bottom guide blocks 59, 59. These guide blocks 59, 59 have therebetween an interval that is the same size as or an interval slightly greater than the thickness of one sheet of the pulp sheet, and the tip end 3LE of the pulp sheet 3 is sent through this interval to a position close to the rotating blade 22 of the crusher 20. Here, with these guide blocks 59, 59, the pulp sheet 3 is restricted to a state in which it cannot move in the thickness direction in a section close to the reeling-out tip end 3LE, therefore the up and down fluttering of the pulp sheet 3 when it is being scraped and crushed with the rotating blade 22 of the crusher 20 is effectively suppressed. As a result, the crushing of the pulp sheet 3 can be stably performed.

By the way, the series of the reeling-out operations of the pulp sheet 3, including switching of the supply of the pulp sheet 3 between these sheet supplying mechanisms 50, 50, is controlled by a PLC 60 (programmable logic controller) as the controller.

Namely, the PLC 60 sends a command value Vpa of a reeling-out speed Vp (m/second) to an amplifier of the servomotor of the pinch rolls 55, and the amplifier drives the servomotor so that, based on the command value Vpa, the deviation between the peripheral speed Vp (m/second) of the pinch rolls 55 and the command value Vpa becomes small, and thus, the reeling-out operation of the pulp sheet 3 is controlled.

In controlling the reeling-out operation, a peripheral speed signal showing the peripheral speed Vd (m/second) that is a rotating speed of the rotating drum 32 is sent to the PLC 60 from the fiber stacking device 30. Namely, the fiber stacking device 30 has a rotating drum speed sensor (not shown) that measures the peripheral speed Vd of the rotating drum 32, and the peripheral speed signal is sent in real-time from the speed sensor to the PLC 60. Then, based on this peripheral speed signal, the PLC 60 changes the command value Vpa of the reeling-out speed (m/second) of the pulp sheet 3, namely the command value Vpa of the peripheral speed Vp (m/second) of the pinch rolls 55, in conjunction with the peripheral speed Vd of the rotating drum 32. In this way, irrespective of the change in the peripheral speed Vd of the rotating drum 32 of the fiber stacking device 30, an appropriate amount of pulp fiber 4 necessary for producing the absorbent body 1 of a predetermined thickness can be sent from the crusher 20 to the fiber stacking device 30 at all times.

For example, in the case of a steady supplying state in which the supply of the pulp sheet 3 is not being switched, that is, in the case that only one sheet supplying mechanism 50 is in a supplying state, and the other sheet supplying mechanism 50 is in a waiting state, when the peripheral speed Vd of the rotating drum 32 is at a predetermined prescribed speed Vdk, the PLC 60 rotatingly controls the above pinch rolls 55 in the supplying state with the predetermined prescribed speed Vpk as the command value, and thus the pulp sheet 3 is set to be reeled out at the prescribed speed Vpk. Then, when the peripheral speed Vb of the rotating drum 32 becomes a speed Vd faster than the prescribed speed Vdk, in order to increase the peripheral speed Vp of the pinch rolls 55 to greater than the prescribed speed Vpk, the PLC 60 raises the command value Vpa of the peripheral speed Vp with the increasing ratio Ra of the rotating drum (=Vd/Vdk) as a proportionality constant (Vpa=Ra×Vpk). On the other hand, when the peripheral speed Vd of the rotating drum 32 becomes a slower speed Vd than the prescribed speed Vdk, in order to decrease the peripheral speed Vp of the pinch rolls 55 to slower than the prescribed speed Vpk, the PLC 60 lowers the command value Vpa of the peripheral speed Vp with the decreasing ratio Ra of the rotating drum 32 (=Vd/Vdk) as a proportionality constant (Vpa=Ra×Vpk). In this way, irrespective of the change in the peripheral speed Vd of the rotating drum 32 of the fiber stacking device 30, an appropriate amount of the pulp fibers 4 necessary for producing the absorbent body 1 of a predetermined thickness can be sent from the crusher 20 to the fiber stacking device 30 at all times.

Note that, below, the command value Vpa of the reeling-out speed Vp (peripheral speed Vp of the pinch rolls 55) of the pulp sheet 3 necessary for producing a predetermined thickness during the above steady supplying is also referred to as a steady reeling-out speed Vs (corresponds to a reference speed). Note that, this steady reeling-out speed Vs, as described above, changes corresponding to the peripheral speed Vd of the rotating drum 32, and the PLC 60 obtains the steady reeling-out speed Vs in real-time by performing the above-mentioned computation and the like based on the peripheral speed signal from the rotating drum speed sensor.

Figure 5:
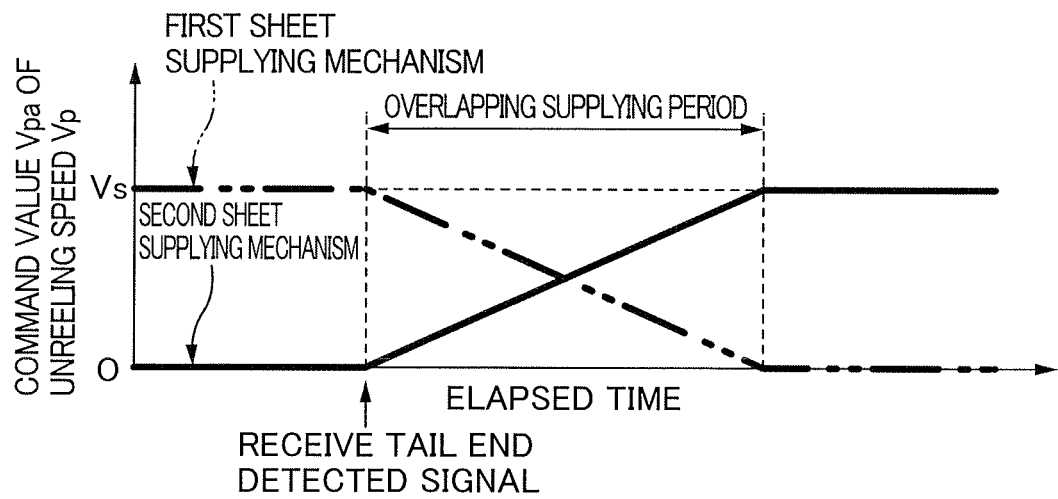
FIG. 5 is a timing line drawing of a switching operation of switching the supply operation of the pulp sheet 3 from one sheet supplying mechanism 50 to another sheet supplying mechanism 50.

FIG. 5 is a timing line figure of a switching operation of switching the supply of the pulp sheet 3 to the crusher 20 from a supplying sheet supplying mechanism 50 to a waiting sheet supplying mechanism 50. In the graph in FIG. 5, an elapsed time is shown in a horizontal axis and a command value Vpa of the reeling-out speed Vp is shown in a vertical axis.

In this first embodiment, in the switching operation, the PLC 60 controls the rotation of the pinch rolls 55, 55 of both sheet supplying mechanisms 50, 50, so that the supply amount of the pulp sheet 3 corresponding to the above-mentioned steady reeling-out speed Vs is maintained on the whole. Thus, during the switching, the fluctuations in the supply amount of the pulp sheet 3 to the crusher 20 are suppressed. This is described in detail below.

This switching operation starts when detecting with a sensor that the end of reeling out the pulp sheet roll 5 with the supplying sheet supplying mechanism 50 is close. Thus, as shown in FIG. 4, each of the sheet supplying mechanisms 50 is provided with a tail end detector sensor 65 that detects that the tail end 3TE of the pulp sheet roll 5 has come off the core rod 53 of the reel 52, for example. The tail end detector sensor 65 is, for example, a phototube or the like, and the sensor is provided in between the pinch rolls 55 and the core rod 53 of the reel 52. Then, based on change in the light-receiving state or the like when the tail end 3TE has passed the set position of the sensor 65, whether or not the tail end 3TE has passed is detected, and the tail end detection signal is sent to the PLC 60.

Note that, the sensor is not limited in any way to the above-mentioned tail end detector sensor 65, and a sensor that can detect that the end of reeling out the pulp sheet roll 5 that is being supplied is near is applicable. For example, the sensor may be a sensor that is arranged close to the end surface of the pulp sheet roll 5 and that sends a detected signal of the end of the reeling out to the PLC 60, based on the change in a diameter of the pulp sheet roll 5 (for example, when the diameter reduced in diameter in accordance with the reeling out becomes smaller than a desired threshold, or the sensor can be a sensor that successively measures an angular speed (rad/second) of the pulp sheet roll 5 and that sends the detected signal to the PLC 60 when the angular speed has exceeded a threshold of a desired angular speed.

Then, the PLC 60 that has received the tail end detected signal from the tail end detector sensor 65 controls the servomotor of the pinch rolls 55 of the sheet supplying mechanism 50 that is supplying and the servomotor of the pinch rolls 55 of the sheet supplying mechanism 50 that is waiting as below, and switches the supplying operation of the pulp sheet 3 to the crusher 20 from the sheet supplying mechanism 50 that is supplying to the sheet supplying mechanism 50 that is waiting.

Note that, below, for the sake of convenience, the sheet supplying mechanism 50 that is supplying is referred to as a "first sheet supplying mechanism 50", and the sheet supplying mechanism 50 that is waiting is referred to as a "second sheet supplying mechanism 50". Similarly, the pinch rolls 55 of the sheet supplying mechanism 50 that is supplying are referred to as "first pinch rolls 55" and the pinch rolls 55 of the sheet supplying mechanism 50 that is waiting are referred to as "second pinch rolls 55". The terms "first" and "second" that are used as described above are used similarly for other structures, for example, for the "pulp sheet 3" and the "pulp sheet roll 5".

First, as shown in FIG. 4, when the reeled-up remaining amount of the supplying pulp sheet roll 5, namely the first pulp sheet roll 5, becomes small, and the tail end 3TE of the first pulp sheet 3 comes off the core rod 53 of the reel 52, and the tail end 3TE passes the set position of the tail end detector sensor 65, the tail end detector sensor 65 detects the above and sends the tail end detected signal to the PLC 60. Then, the PLC 60 starts the switching operation.

As shown in FIG. 5, in this switching operation, there is an overlapping supplying period (corresponds to a predetermined period) in which the supply of the pulp sheet 3 from both the first sheet supplying mechanism 50 and the second sheet supplying mechanism 50 to the crusher 20 overlap. Then, in this overlapping supplying period, the PLC 60 decreases the reeling-out speed Vp of the first pulp sheet roll 5 that was supplying at a steady reeling-out speed Vs from the steady reeling-out speed Vs to zero, and at the same time, the reeling-out speed Vp of the second pulp sheet roll 5 that was waiting is increased from zero to the steady reeling-out speed Vs. In this way, the supplying operation is switched from the first sheet supplying mechanism 50 to the second sheet supplying mechanism 50.

Further, in this overlapping supplying period, the PLC 60 controls the rotations of the first and second pinch rolls 55, 55 so that the sum of the reeling-out speed Vp of the first sheet supplying mechanism 50 and the reeling-out speed Vp of the second sheet supplying mechanism 50 is within a range of ±10% of the steady reeling-out speed Vs. More preferably, the rotations of the pinch rolls are controlled to be in a range of ±5%, and further more preferably the rotations are controlled to be the same value as the steady reeling-out speed Vs. Therefore, during the switching of the supply, the supply amount of the pulp sheets 3, 3 to be supplied to the crusher 20 is generally maintained as the supply amount of the pulp sheet 3 corresponding to the above-mentioned steady reeling-out speed Vs. As a result, during the switching, an appropriate amount of the pulp fibers 4 necessary to produce the absorbent body 1 of a desired thickness is to be sent from the crusher 20 to the fiber stacking device 30.

Below is given an example of a specific method of control to make the sum of the reeling-out speed Vp of the first sheet supplying mechanism 50 and the reeling-out speed Vp of the second sheet supplying mechanism 50 be in a predetermined range of the steady reeling-out speed Vs in this way.

First, the command value Vpa of the reeling-out speed Vp of the first sheet supplying mechanism 50 is made by multiplying the above-described steady reeling-out speed Vs with a ratio Rb of a numerical value from 0 to 1 (a decimal fraction including 0 and 1), and the command value Vpa of the reeling-out speed Vp of the second sheet supplying mechanism 50 is made by multiplying the steady reeling-out speed Vs with 1-Rb. Then, by gradually decreasing the ratio Rb in the overlapping supplying period from 1 to zero, the command value Vpa of the reeling-out speed Vp of the first sheet supplying mechanism 50 changes in a speed pattern that gradually decreases from the steady reeling-out speed Vs to zero as in FIG. 5, and the command value Vpa of the reeling out pattern Vp of the second sheet supplying mechanism 50 changes in a speed pattern that gradually increases from 0 to the steady reeling-out speed Vs. Then, after this switching operation, the ratio Rb is maintained at "1" until the next switching operation.

Figure 6:
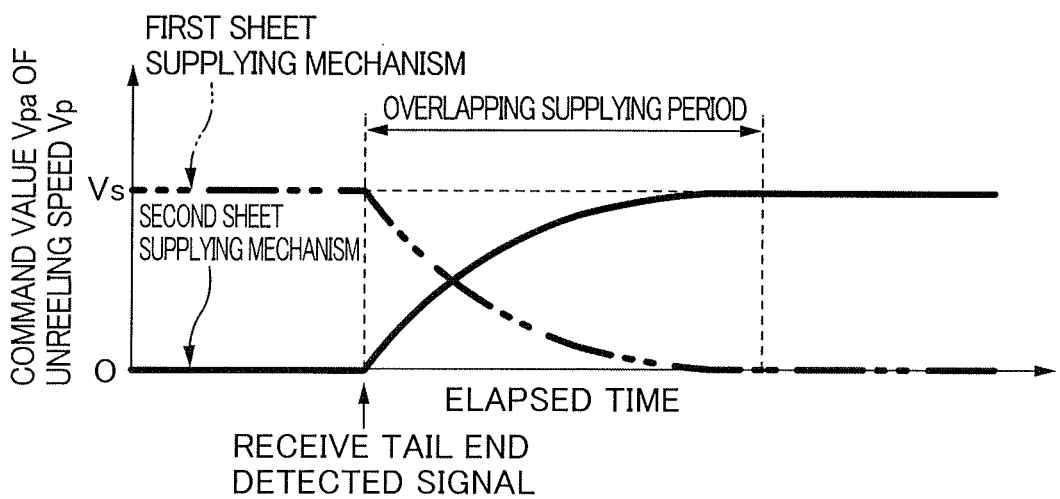
FIG. 6 is another example of the same timing line drawing.

Note that, the changing pattern of the command value Vpa of the reeling-out speed Vp in the overlapping supplying period is changeable to an arbitrary pattern by setting to a changing pattern with the above ratio Rb. For example, as shown in FIG. 5, in the case that the command value Vpa of the reeling-out speed Vp is to be changed linearly in respect to the elapsed time, the ratio Rb may be changed linearly from 1 to zero in respect to the elapsed time, or as shown in FIG. 6 in the case that the command value Vpa is to be changed non-linearly by a curved line or the like of an exponential function in respect to the elapsed time, the ratio Rb may be changed non-linearly from 1 to zero in respect to the elapsed time.

Further, in the above description, the PLC 60 started the switching operation with the receiving time of the tail end detected signal as a starting point, but it is not limited to this, and the switching operation may be started by being delayed by only a predetermined time from the above receiving time.

Further, before receiving the detected signal, namely before the above-mentioned switching operation is started, the reeling-out tip end 3LE of the second pulp sheet 3 is set in a desired setting position near the tip end of the guide blocks 59 in advance, and therefore it is needless to say that the reeling-out tip end 3LE is set in a state substantially in contact with the rotating blade 22 of the crusher 20 (refer to the upper sheet supplying mechanism 50 in FIG. 4). The position of the reeling-out tip end 3LE, however, can be slightly shifted to the pinch roll 55 side than the above setting position. This is because the supply amount of the second pulp sheet 3 to the crusher 20 when starting the switching is much smaller than the supply amount of the first pulp sheet 3, as is clear from FIG. 5, and in view of this even in the case that the position of the tip end 3LE of the second pulp sheet 3 is shifted somewhat to the front or behind, it hardly affects the supply amount of the pulp sheet 3 to the crusher 20.

Here, preferably, before the tail end 3TE of the first pulp sheet 3 passes the setting position of the first pinch rolls 55 of the first sheet supplying mechanism 50, the above switching operation may be set so that the reeling-out speed Vp of the first pinch rolls 55 becomes zero and the rotations of the first pinch rolls are stopped.

In this way, the above-mentioned pull-in phenomenon of the pulp sheet 3 to the crusher 20 (a phenomenon that, after the tail end 3TE of the pulp sheet 3 passes the pinch rolls 55, the pulp sheet 3 is rapidly pulled in to the crusher 20 side with the rotating blade of the crusher 20) can be prevented, and as a result the fluctuations in the supply amount of the pulp sheet 3 to the crusher 20 can be suppressed. This setting can be performed by adjusting and the like the setting position of the tail end detector sensor 65.

Further, preferably, the PLC 60 may control the first pinch rolls 55 so that they rotate in a reverse direction after the rotation of the above-mentioned first pinch rolls 55 have stopped. In this way, the remaining material of the first pulp sheet 3, that is in a state sandwiched between the first pinch rolls 55, 55 can be transported in a reverse direction to the reeling-out direction of the sheet 3, namely can be reversely transported to the reel 52 side. In this way, the remaining material can be discharged out of the device safely and easily.

Further, preferably, the time length of the above-mentioned the overlapping supplying period may be equal to or greater than 2 seconds and equal to or smaller than 20 seconds. In that case, based on that the time length is equal to or greater than two seconds, the increasing time to increase the second pulp sheet roll 5, namely the pulp sheet roll 5 that is waiting to the steady reeling-out speed Vs can be surely ensured, and in this way the normally used pulp sheet roll 5 of a one ton-grade can be increased with the pinch rolls 55 without any problem of torque deficiency and the like. Further, since the time length is equal to or less than 20 seconds, productivity will not drop drastically.

Second Embodiment

Figure 7:
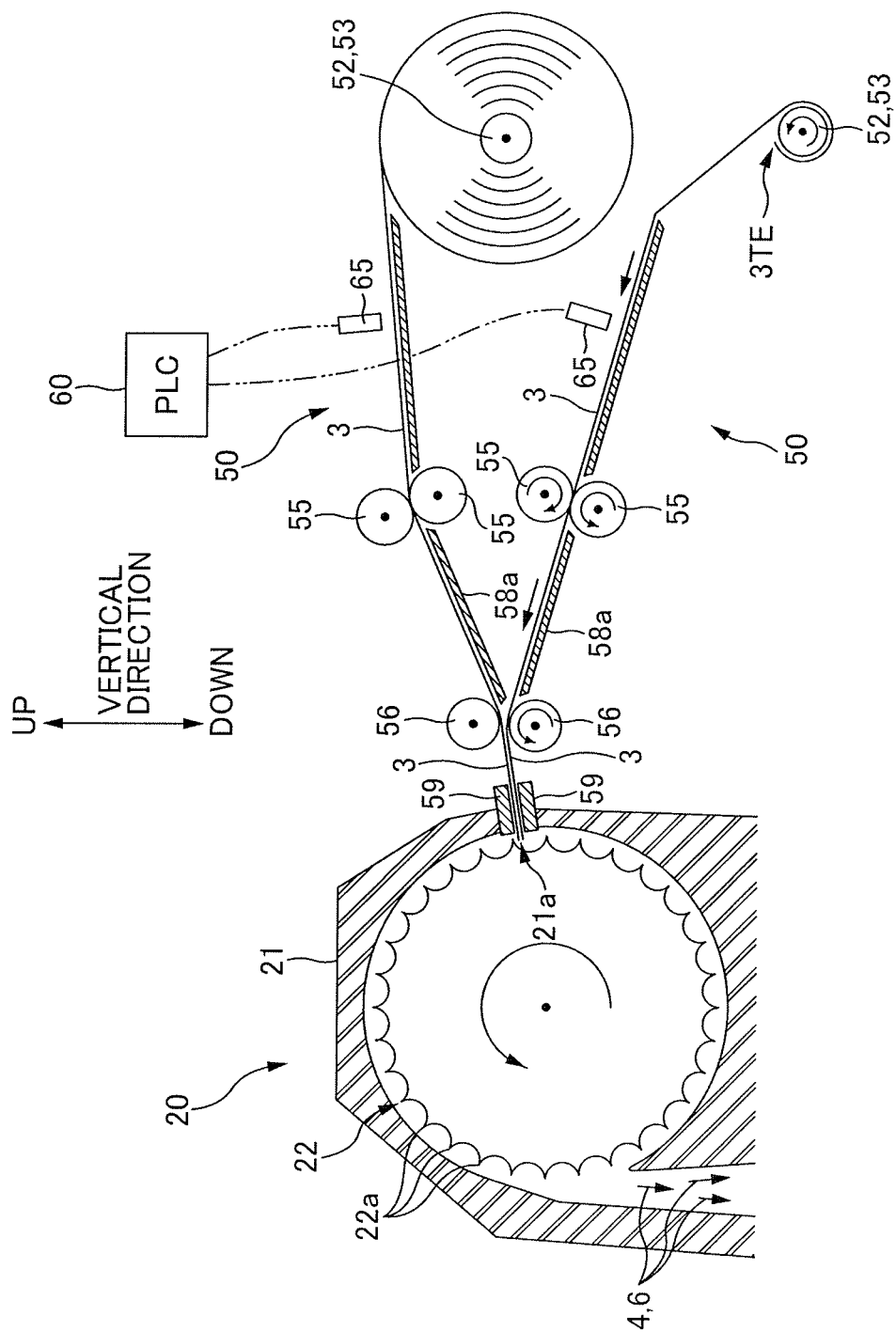
FIG. 7 is a schematic side view of sheet supplying mechanisms 50, 50 of a Second Embodiment.

FIG. 7 is a schematic side view of the sheet supplying mechanisms 50, 50 of a second embodiment.

In the above-mentioned first embodiment, as shown in FIG. 4, the casing 21 of the crusher 20 is provided with a placing opening 21a to each of the first sheet supplying mechanism 50 and the second sheet supplying mechanism 50, and each placing opening 21a is set with each of the pair of top and bottom guide blocks 59, 59.

In respect to this, in the second embodiment in FIG. 7, only one placing opening 21a is provided to both the first sheet supplying mechanism 50 and the second sheet supplying mechanism 50, namely, this embodiment is different from the first embodiment in that one placing opening 21a is shared by these two sheet supplying mechanisms 50, 50. Note that, other than the above point, this embodiment is generally similar to the first embodiment, and below is described only such a difference, and the same structures will have the same reference signs and their description will be omitted.

As shown in FIG. 7, the casing 21 of the crusher 20 is provided with only one placing opening 21a of the pulp sheet 3. This placing opening 21a is arranged with only one pair of top and bottom guide blocks 59, 59, and the guide blocks 59, 59 are shared by both the first sheet supplying mechanism 50 and the second sheet supplying mechanism 50.

Here, the size of the interval between the top and bottom guide blocks 59, 59 is set to the same size or slightly wider than the thickness of two sheets of pulp sheets. In this way, when switching the supply of the sheet supplying mechanisms 50, the guide blocks are designed so that even in a state in which two pulp sheets 3, 3 lie on top of each other in the thickness direction the pulp sheets can pass without a large resistance. Namely, even in the case that the pulp sheets are in a state lying on top of each other and they are each reeled out from each sheet supplying mechanism 50, 50 at different reeling-out speeds Vp, Vp from each other, a relative slip between the pulp sheets 3, 3 are allowed.

Note that, a pair of top and bottom guide rolls 56, 56 is set in a position near to the guide blocks 59 on the transporting path of the pulp sheets 3 between the guide blocks 59 and the pinch rolls 55. These guide rolls 56, 56 are arranged rotatably around a rotational axis along the CD direction, and the size of the roll interval between the guide rolls 56, 56 is set to a size greater than a thickness of two pulp sheets and equal to or less than five times the thickness of the two sheets. Each of the sheet supplying mechanisms 50, 50 is arranged with guide plates 58a, 58a that extend from the roll interval between the pinch rolls 55, 55 to the roll interval between the guide rolls 56, 56, and with this each of the pulp sheets 3, 3 sent out from each of the first and second pinch rolls 55, 55 are guided to reach the roll interval between the guide rolls 56, 56. Therefore, both the first pulp sheet 3 of the first sheet supplying mechanism 50 and the second pulp sheet 3 of the second sheet supplying mechanism 50 are guided smoothly to the guide blocks 59, 59 and crushed with the crusher 20.

By the way, the guide rolls 56 may be follower rolls that run freely by contacting with the pulp sheet 3, or the rolls may be driving rolls that drivingly rotate the pulp sheets 3 in the supplying direction, by obtaining a rotating force from an appropriate driving source such as a motor.

Then, with a structure in which there is one placing opening 21a, the difference in the crushing degree of the pulp sheets 3 due to the difference between the first and second sheet supplying mechanisms 50, 50 can be eliminated, and in this way the quality can be made stable by making the fluctuations in fineness of the pulp fiber 4 small and the like.

Figure 8:
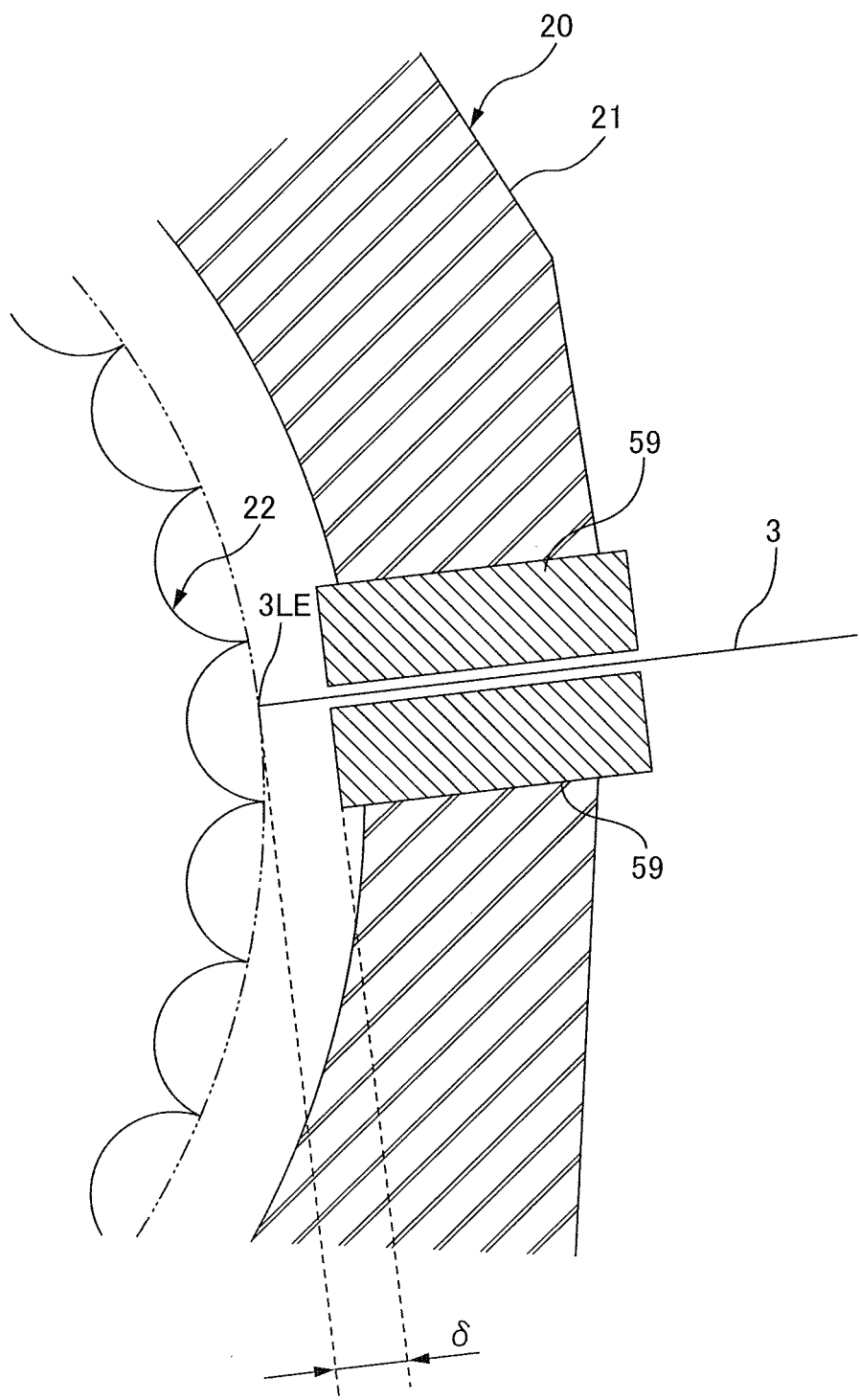
FIG. 8 is an enlarged diagram showing an arrangement relationship of guide blocks 59 and a rotating blade 22 of a crusher 20.

FIG. 8 is an explanatory view of the above and is an enlarged view showing an arrangement relationship of the guide blocks 59 and the rotating blade 22 of the crusher 20.

Generally, the rotating blade 22 of the crusher 20 and the guide blocks 59, 59 are opposed with a predetermined distance δ in between. Then, in a state in which the reeling-out tip end 3LE of the pulp sheet 3 from the guide block 59 to the rotating blade 22 side is projected in a cantilevered state, the reeling-out tip end 3LE is scraped and crushed with the rotating blade 22 that rotates in one direction. Therefore, in accordance with the size of the predetermined distance δ between the rotating blade 22 and the guide blocks 59, the crushing degree of the pulp sheet 3 changes.

In regards to the above point, in the case of the above-mentioned first embodiment, there are two placing openings 21a, and in some cases, there is a possibility that a different predetermined distance δ may be set for each of these placing openings 21a, 21a, and in that case, with the selection of the first or the second sheet supplying mechanism 50, 50 to be used, there is a possibility that the fineness and the like of the pulp fibers 4 may vary for each mechanism.

In regards to the above point, in the case one placing opening 21a is shared as in the second embodiment, the crushing condition of the pulp sheet 3 with the crusher 20 can be made the same for each of the sheet supplying mechanisms 50, 50, and the above-mentioned defect can be prevented in advance.

By the way, in the case of a structure having two placing openings 21a, 21a as in the first embodiment of FIG. 4, in the case that the placing opening 21a for the first sheet supplying mechanism and the placing opening 21a for the second sheet supplying mechanism 50 are designed so that the predetermined distance δ is made to be the same value, the crushing conditions can be made the same, and the fineness of the pulp fibers 4 can be made approximately the same. Thus, the above-described first embodiment is designed in such a way.

Other Embodiments

Above, the embodiments of this invention have been described, but this invention is not limited to the above embodiments, and modifications shown below are possible.

Figure 9:
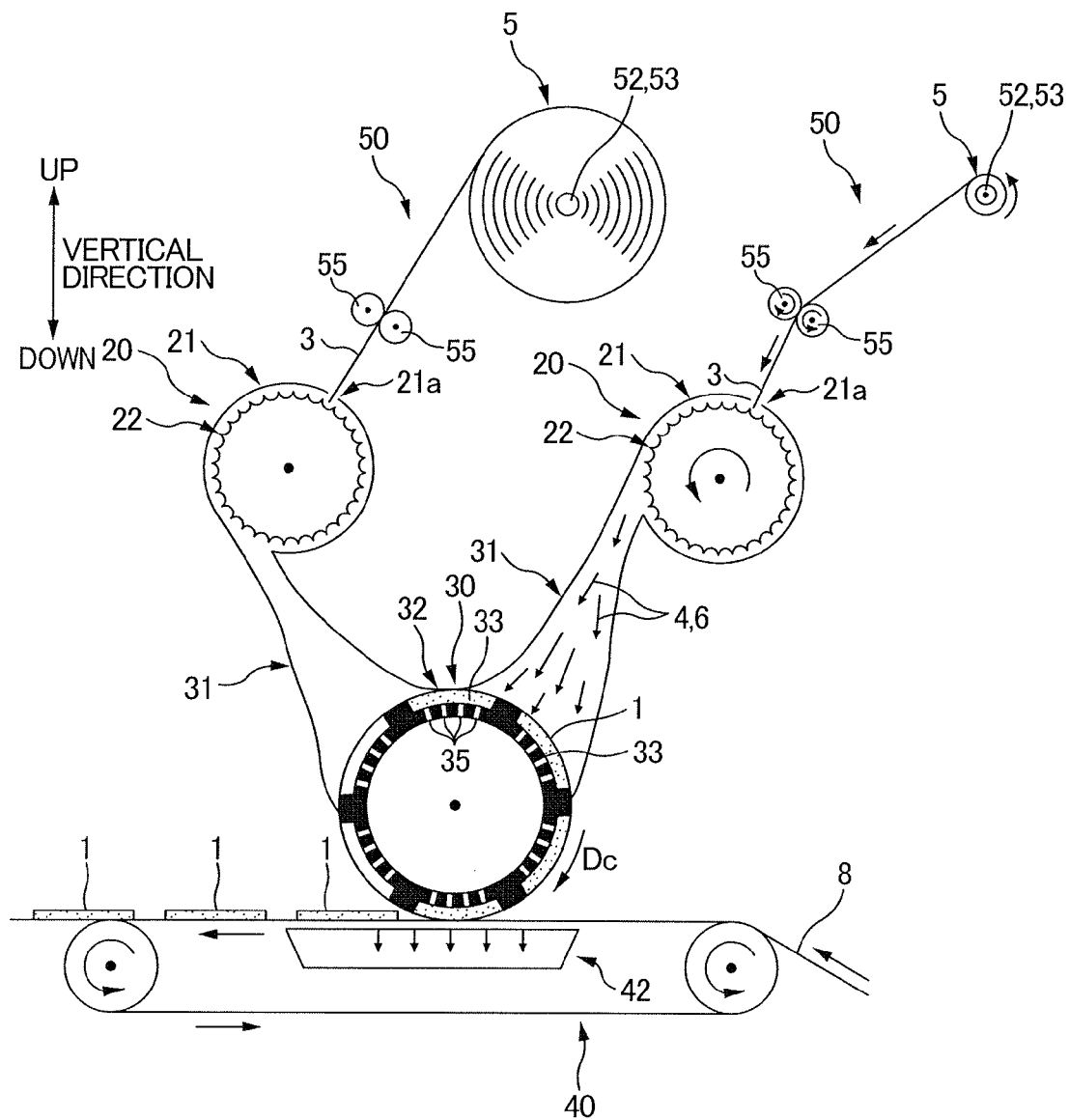
FIG. 9 is a schematic side view of an apparatus that manufactures an absorbent body 1 of another embodiment.

In the above-mentioned embodiments, a structure is illustrated in which one crusher 20 is connected to one fiber stacking device 30, and two sheet supplying mechanisms 50, 50 are provided to the crusher 20, but it is not limited thereto. For example, as in the schematic side view of FIG. 9, two crushers 20, 20 are provided to one fiber stacking device 30, and one sheet supplying mechanism 50 may be provided corresponding to each crusher 20. Then, in this case, the switching of the supplying operation as in the above-mentioned first embodiment is to be performed between these sheet supplying mechanisms 50, 50. Further, the supply of the pulp fibers 4 to the fiber stacking device 30 from each crusher 20 is performed via a duct 31 provided to each crusher 20.

In the above-mentioned embodiments, the pulp sheet 3 is shown as one example of the sheet, and the pulp fiber 4 is shown as one example of the fibrous matter, but it is not limited to this in any way. In the case that the sheet is such that the fibrous matter produced by crushing has an absorbent ability of a liquid such as a waste liquid, such sheet can be used, and the sheet may be a rayon sheet or a cotton sheet, for example, in which case, from each sheet a rayon fiber or a cotton fiber will be produced by crushing as a fibrous matter.

In the above-mentioned embodiments, as shown in FIGS. 5 and 6, when switching, the decreasing starting point of the reeling-out speed Vp of the first sheet supplying mechanism 50 and the increasing starting point of the reeling-out speed Vp of the second sheet supplying mechanism 50 are aligned, and further the point of stopping the reeling out of the first sheet supplying mechanism 50 (the point in which the reeling-out speed Vp becomes zero) and the point that the reeling-out speed Vp of the second sheet supplying mechanism 50 becomes the steady reeling-out speed Vs are aligned, but it is not limited thereto. The above points that correspond to each other may be shifted slightly forwards or backwards. For example, the points may be as shown in FIGS. 10A to 10D.

REFERENCE SIGNS LIST 1 absorbent body, 3 pulp sheet (sheet),
3LE tip end (reeling-out tip end), 3TE tail end,
4 pulp fiber (fibrous matter), 5 pulp sheet roll (sheet roll),
6 air flow, 8 continuous sheet member, 20 crusher,
21 casing, 21a placing opening (opening section),
22 rotating blade, 22a cutting edge,
30 fiber stacking device, 31 duct, 32 rotating drum,
33 shaping die, 35 suction hole,
40 belt conveyor, 42 suction box,
50 sheet supplying mechanism, 52 reel, 53 core rod,
55 pinch roll, 56 guide roll,
58 guide plate, 58a guide plate,
59 guide block, 65 tail end detector sensor (sensor)

The invention claimed is:

1. An apparatus for manufacturing an absorbent body, said apparatus comprising:
a first sheet supplying mechanism configured to reel out and supply a sheet from a sheet roll made by reeling up the sheet in a roll shape, the first sheet supplying mechanism having
a pair of first pinch rolls configured to sandwich the sheet and drivingly rotate to reel out the sheet from the sheet roll, and
a first sensor configured to detect that a tail end of the sheet reeling out from the first sheet supplying mechanism is close;
a second sheet supplying mechanism configured to reel out and supply a sheet from a sheet roll made by reeling up the sheet in a roll shape, the second sheet supplying mechanism having
a pair of second pinch rolls configured to sandwich the sheet and drivingly rotate to reel out the sheet from the sheet roll, and
a second sensor configured to detect that a tail end of the sheet reeling out from the second sheet supplying mechanism is close;
a controller configured to control the driving rotation of the first pinch rolls and the second pinch rolls;
a crusher configured to crush the sheet supplied from the first or second sheet supplying mechanism into a fibrous matter by scraping a lead end of the sheet that has been reeled out from the first or second sheet supplying mechanism; and
a fiber stacking device configured to laminate the fibrous matter sent out from the crusher in a predetermined shape to obtain the absorbent body,
wherein
when switching a supply of the sheet to the crusher from the first sheet supplying mechanism to the second sheet supplying mechanism, the controller is configured to
control the driving rotation of the first pinch rolls such that a reeling-out speed of the sheet from the first sheet supplying mechanism is decreased in a predetermined period, and
control the driving rotation of the second pinch rolls such that a reeling-out speed of the sheet from the second sheet supplying mechanism is increased in the predetermined period.

2. The apparatus according to claim 1, wherein
when the first sensor detects that the tail end of the sheet reeling out from the first sheet supplying mechanism is close to the first pinch rolls, the controller is configured to cause the driving rotation of the first pinch rolls to stop before the tail end of the sheet passes through the first pinch rolls.

3. The apparatus according to claim 2, wherein
the controller, after causing the driving rotation of the first pinch rolls to stop in the predetermined period, is configured to cause the first pinch rolls to rotate in an opposite direction to a rotating direction before the driving rotation stopped.

4. The apparatus according to claim 1, wherein
the crusher includes
a casing,
a rotating blade provided in the casing and configured to scrape the lead end of the sheet that has been reeled out from the first or second sheet supplying mechanism, and
an opening section provided to the casing,
both the first sheet supplying mechanism and the second sheet supplying mechanism are configured to insert the corresponding sheet into the opening section.

5. The apparatus according to claim 1, wherein
in the predetermined period, the controller is configured to
control the driving rotation of the first pinch rolls so that the reeling-out speed of the first sheet supplying mechanism becomes zero by gradually decreasing from a predetermined reference speed, and
control the driving rotation of the second pinch rolls so that the reeling-out speed of the second sheet supplying mechanism becomes the predetermined reference speed by gradually increasing from zero.

6. The apparatus according to claim 5, wherein
in the predetermined period, the controller is configured to control the driving rotation of the first and second pinch rolls so that a sum of the reeling-out speed of the first sheet supplying mechanism and the reeling-out speed of the second sheet supplying mechanism is in a range of ±10% of the predetermined reference speed.

7. The apparatus according to claim 6, wherein
in the predetermined period, the controller is configured to
linearly decrease the reeling-out speed of the first sheet supplying mechanism from the predetermined reference speed to zero, and linearly increase the reeling-out speed of the second sheet supplying mechanism from zero to the predetermined reference speed.

8. The apparatus according to claim 6, wherein
in the predetermined period, the controller is configured to
non-linearly decrease the reeling-out speed of the first sheet supplying mechanism from the predetermined reference speed to zero, and
non-linearly increase the reeling-out speed of the second sheet supplying mechanism from zero to the predetermined reference speed.

9. The apparatus according to claim 1, wherein
the predetermined period starts in response to a detection signal issued by the first sensor when the first sensor detects that the tail end of the sheet reeling out from the first sheet supplying mechanism is close to the to the first pinch rolls.

10. The apparatus according to claim 9, wherein
in the predetermined period, the controller is configured to decrease the reeling-out speed of the first sheet supplying mechanism after increasing the reeling-out speed of the second sheet supplying mechanism.

11. The apparatus according to claim 10, wherein
in the predetermined period, the controller is configured to
decrease the reeling-out speed of the first sheet supplying mechanism from a predetermined reference speed to zero, and
increase the reeling-out speed of the second sheet supplying mechanism from zero to the predetermined reference speed, and
control the reeling-out speed of the first sheet supplying mechanism to reach zero before the reeling-out speed of the second sheet supplying mechanism reaches the predetermined reference speed.

12. The apparatus according to claim 10, wherein
in the predetermined period, the controller is configured to
decrease the reeling-out speed of the first sheet supplying mechanism from a predetermined reference speed to zero, and
increase the reeling-out speed of the second sheet supplying mechanism from zero to the predetermined reference speed, and
control the reeling-out speed of the first sheet supplying mechanism to reach zero after the reeling-out speed of the second sheet supplying mechanism reaches the predetermined reference speed.

13. The apparatus according to claim 9, wherein
in the predetermined period, the controller is configured to
decrease the reeling-out speed of the first sheet supplying mechanism before increasing the reeling-out speed of the second sheet supplying mechanism.

14. The apparatus according to claim 13, wherein
in the predetermined period, the controller is configured to
decrease the reeling-out speed of the first sheet supplying mechanism from a predetermined reference speed to zero, and
increase the reeling-out speed of the second sheet supplying mechanism from zero to the predetermined reference speed, and
control the reeling-out speed of the first sheet supplying mechanism to reach zero before the reeling-out speed of the second sheet supplying mechanism reaches the predetermined reference speed.

15. The apparatus according to claim 13, wherein
in the predetermined period, the controller is configured to
decrease the reeling-out speed of the first sheet supplying mechanism from a predetermined reference speed to zero, and
increase the reeling-out speed of the second sheet supplying mechanism from zero to the predetermined reference speed, and
control the reeling-out speed of the first sheet supplying mechanism to reach zero after the reeling-out speed of the second sheet supplying mechanism reaches the predetermined reference speed.

16. The apparatus according to claim 1, wherein
the first sensor is arranged upstream of the first pinch rolls in a reeling-out direction in which the first sheet supplying mechanism is configured to reel-out the corresponding sheet, and
the second sensor is arranged upstream of the second pinch rolls in a reeling-out direction in which the second sheet supplying mechanism is configured to reel-out the corresponding sheet.

* * * * *